United States Patent
Denyer et al.

[11] Patent Number: 6,116,233
[45] Date of Patent: Sep. 12, 2000

[54] DRUG DELIVERY ARRANGEMENT

[75] Inventors: Jonathan Stanley Harold Denyer, Chichester; Kevin McGuinness, Stalybridge, both of United Kingdom

[73] Assignee: Medic-Aid Limited, Sussez, United Kingdom

[21] Appl. No.: 08/396,277

[22] Filed: Feb. 28, 1995

Related U.S. Application Data

[63] Continuation of application No. 08/117,402, Sep. 3, 1993, abandoned.

[30] Foreign Application Priority Data

Sep. 11, 1992 [GB] United Kingdom .................... 9219327

[51] Int. Cl.$^7$ .................................................. A61M 11/00
[52] U.S. Cl. ............................... 128/200.18; 128/203.12; 128/204.26
[58] Field of Search ..................... 128/200.14, 200.18, 128/203.12, 204.23, 204.26

[56] References Cited

U.S. PATENT DOCUMENTS

| | | | |
|---|---|---|---|
| 3,777,742 | 12/1973 | Aumiller et al. | 128/203.15 |
| 3,789,843 | 2/1974 | Armstrong et al. | 128/173 |
| 3,812,854 | 5/1974 | Michaels et al. | 128/194 |
| 4,106,503 | 8/1978 | Rosenthal et al. | 128/200.18 |
| 4,109,656 | 8/1978 | Goethel et al. | 128/203.15 |
| 4,253,468 | 3/1981 | Lehmbeck | 128/200.18 |
| 4,263,907 | 4/1981 | Lindsey | 128/200.18 |
| 4,396,015 | 8/1983 | Johnson | 128/200 |
| 4,429,835 | 2/1984 | Brugger et al. | 128/200.18 |
| 4,462,397 | 7/1984 | Suzuki | 128/200.18 |
| 4,612,928 | 9/1986 | Tiep et al. | 128/204.23 |
| 4,649,911 | 3/1987 | Knight et al. | 128/203.15 |
| 4,677,975 | 7/1987 | Edgar et al. | 128/200.14 |
| 4,938,212 | 7/1990 | Snook et al. | 128/205.24 |
| 4,955,371 | 9/1990 | Bamba et al. | 128/200.18 |
| 5,186,164 | 2/1993 | Raghuprasad | 128/203.15 |
| 5,186,166 | 2/1993 | Riggs et al. | 128/203.15 |
| 5,195,528 | 3/1993 | Hok | 128/204.23 |

FOREIGN PATENT DOCUMENTS

| | | |
|---|---|---|
| 0 414 536 A3 | 2/1971 | European Pat. Off. . |
| 0 178 925 | 4/1986 | European Pat. Off. . |
| 0 186 280 | 7/1986 | European Pat. Off. . |
| 0387222 | 12/1990 | European Pat. Off. . |
| 0461281A1 | 12/1991 | European Pat. Off. ........ A61B 5/087 |
| 2164569 | 3/1986 | United Kingdom ............. 128/203.12 |
| 2204799 | 1/1988 | United Kingdom . |
| 8606969 | 12/1986 | WIPO ............................... 128/203.12 |
| 8702577 | 5/1987 | WIPO ............................... 128/204.23 |
| WO87/04384 | 7/1987 | WIPO . |
| WO 89/06147 | 7/1989 | WIPO ........................... A61M 15/00 |
| WO89/06147 | 7/1989 | WIPO . |
| WO913327 | 11/1990 | WIPO . |
| WO92/09323 | 6/1992 | WIPO . |

OTHER PUBLICATIONS

*Textbook of Respiratory Medicine*, vol. 1, $2^{nd}$ ed., Murray et al, W.B. Saunders Company, ISBN #0721638902.

*Primary Examiner*—Aaron J. Lewis
*Attorney, Agent, or Firm*—Christensen O'Connor Johnson & Kindness PLLC

[57] ABSTRACT

An arrangement for delivering a drug aerosol comprises a sensor (3) which detects turbulent air flow during inhalation and causes the nebulizer (8,9,10,11,12,13) to generate the aerosol only during the inhalation phase of the breathing cycle. Airflow is diverted from the sensor during exhalation.

10 Claims, 7 Drawing Sheets

DRUG DELIVERY ARRANGEMENT

This application is a continuation application based on prior application Ser. No. 08/117,402, filed on Sep. 3, 1993 now abandoned.

The present invention relates to a delivery arrangement for delivering a drug aerosol to the respiratory system of a patient.

It is desirable for such a drug delivery arrangement to generate a drug aerosol selectively during inhalation, so that the drug is not wasted during exhalation. It has previously been proposed to make a drug delivery device in which the aerosol of the drug is formed periodically at the same rate as the normal breathing rate, but such a device requires the patient to coordinate his breathing with the periodic drug delivery. However, in many cases patients are not able to coordinate their breathing in this way. Furthermore, other proposed devices for delivering drug to the respiratory system require an increased respiratory flow which, in practice, cannot always be achieved, e.g. by children, especially during an asthma attack.

An object of the present invention is to overcome or alleviate the above problems.

Accordingly the invention provides a drug delivery arrangement for delivering a drug aerosol to the respiratory system of a patient, comprising nebulizer means arranged to generate a drug aerosol in the air stream inhaled by the patient, sensor means responsive to the air flow due to the breathing of the patient, and control means responsive to a control signal generated by said sensor means to cause said nebulizer means to generate said aerosol selectively during the inhalation phase of the patient's breathing cycle.

Preferably the sensor means is responsive to turbulence in said air flow and may comprise a microphone, for example.

Preferred embodiments of the invention are described below by way of example with reference to FIGS. 1 to 6 of the accompanying drawings wherein.

Figure 1:
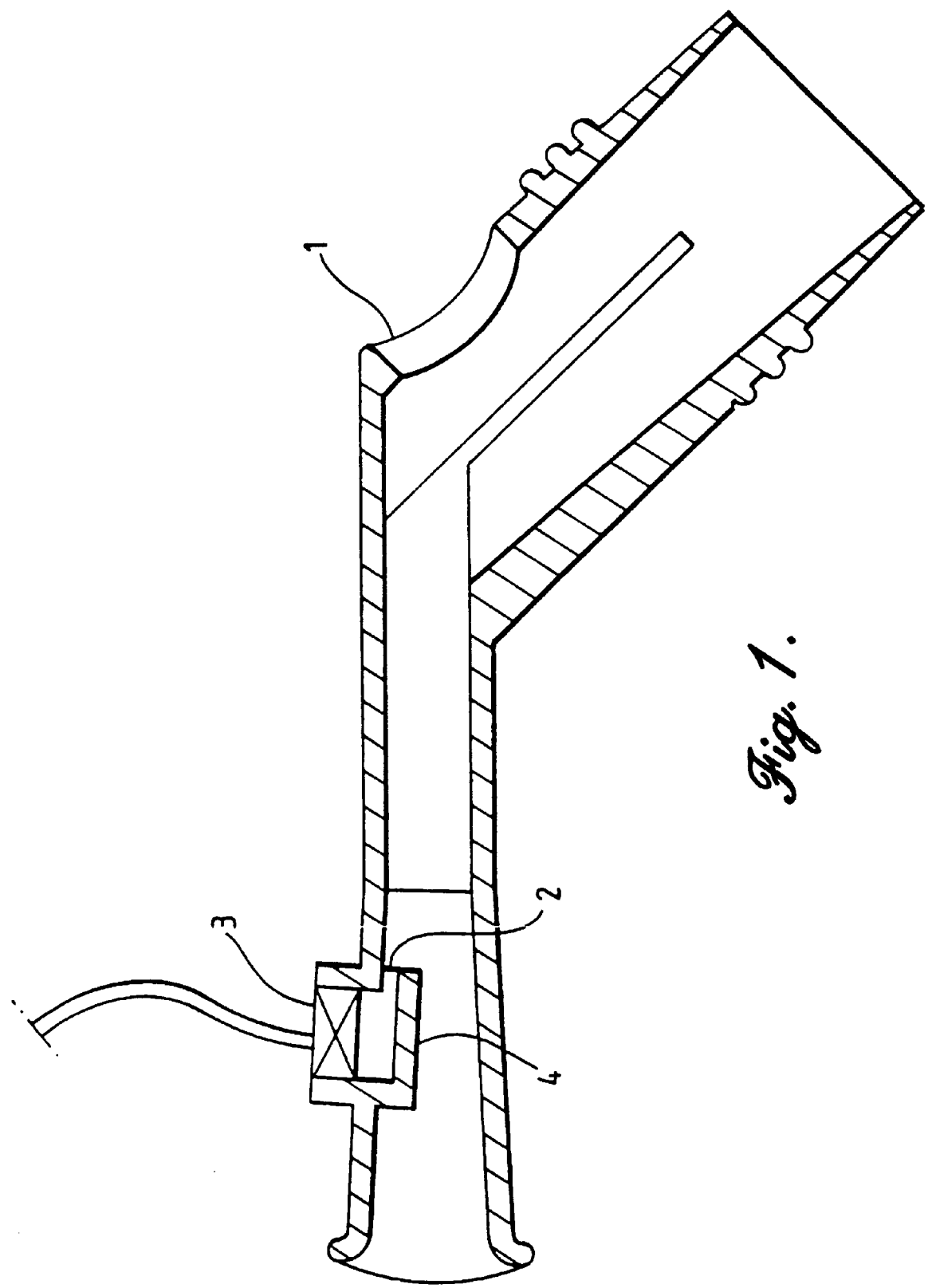
FIG. 1 is a cross-section showing a mouth piece having a sensor mounted therein for use in one embodiment of the invention.

FIG. 1 shows a mouthpiece for use in one embodiment of the invention which comprises a microphone 3 located in a chamber 4 which has an aperture 2 communicating with the air flow through the mouthpiece and directed approximately parallel to the access of the air flow. Consequently, turbulence is generated around the aperture 2 during inhalation (i.e. the air flows from left to right in FIG. 1) whereas little, if any, turbulence is generated during exhalation (when the air flow is in the direction from right to left in FIG. 1). An output from the microphone is connected to a control circuit (such as that described below with reference to FIG. 6) which controls the operation of a nebulizer (not shown) which can be inserted into a port 1 in the mouthpiece. The nebulizer may be of the type shown in GB 838453 and GB 1283988.

The nebulizer is arranged to generate an aerosol of finely divided drug particles (0.5 to 5 micro meters for bronchial deposition and 0.5 to 2 micro meters for alveolar deposition) during each inhalation phase of the breathing cycle. The nebulizer may be arranged to generate a predetermined amount of aerosol for a predetermined number of breathing cycles, thereby enabling a predetermined amount of drug to be delivered.

Figure 2:
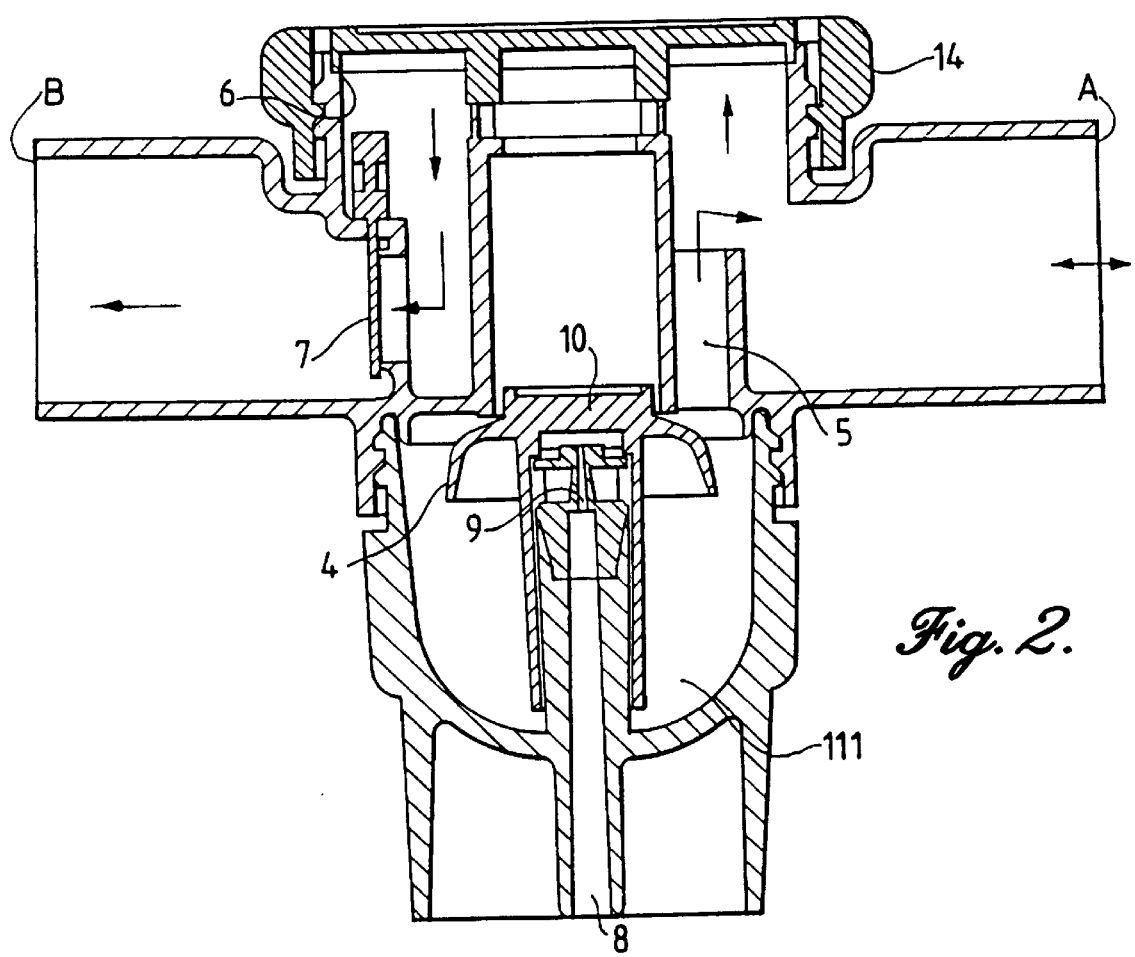
FIG. 2 is an axial cross-section of a valved delivery system for use in an alternative embodiment of the invention.
Figure 3:
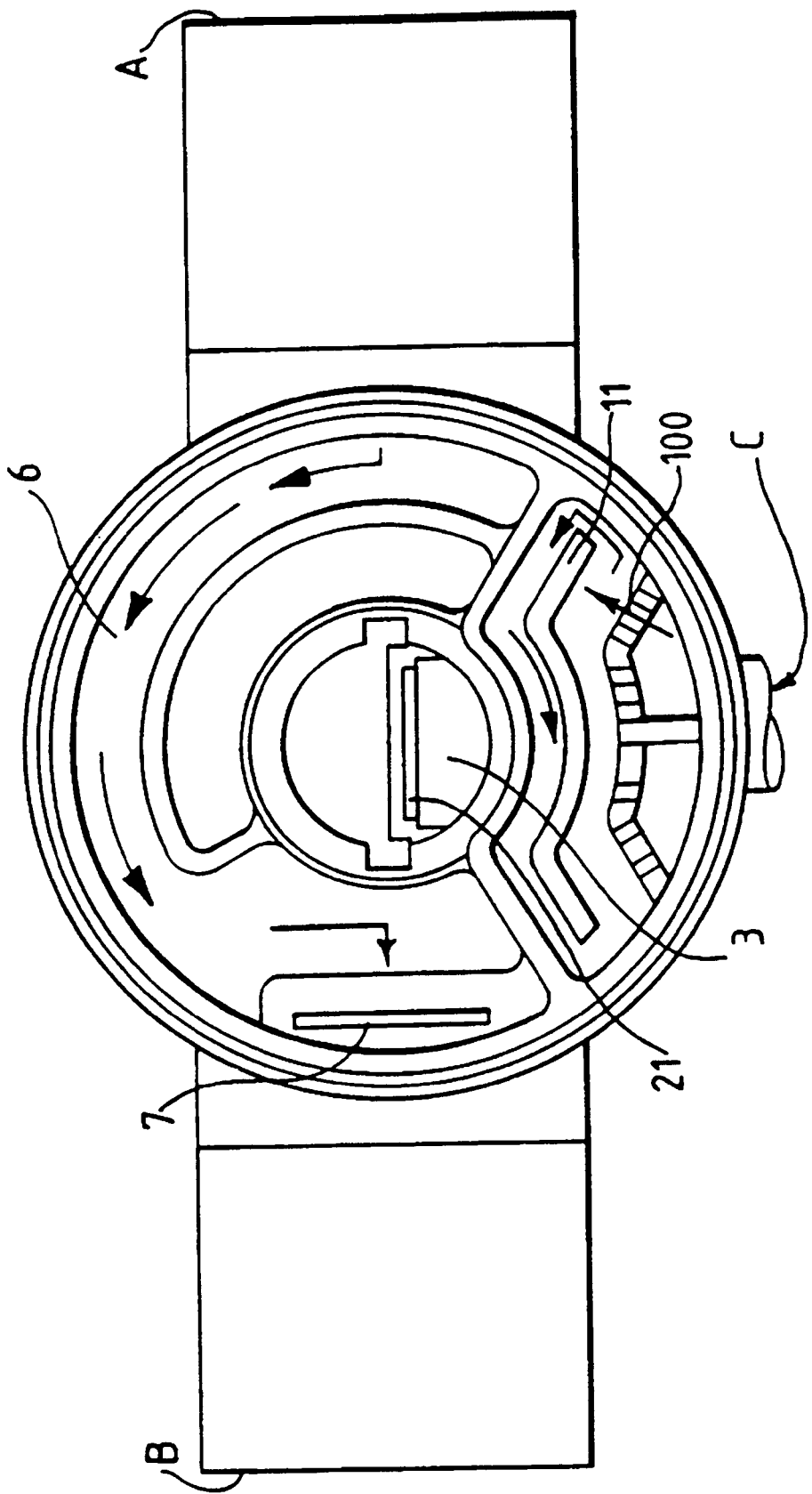
FIG. 3 is a plan view of the delivery system shown in FIG. 2 (with the top cap removed)
Figure 4:
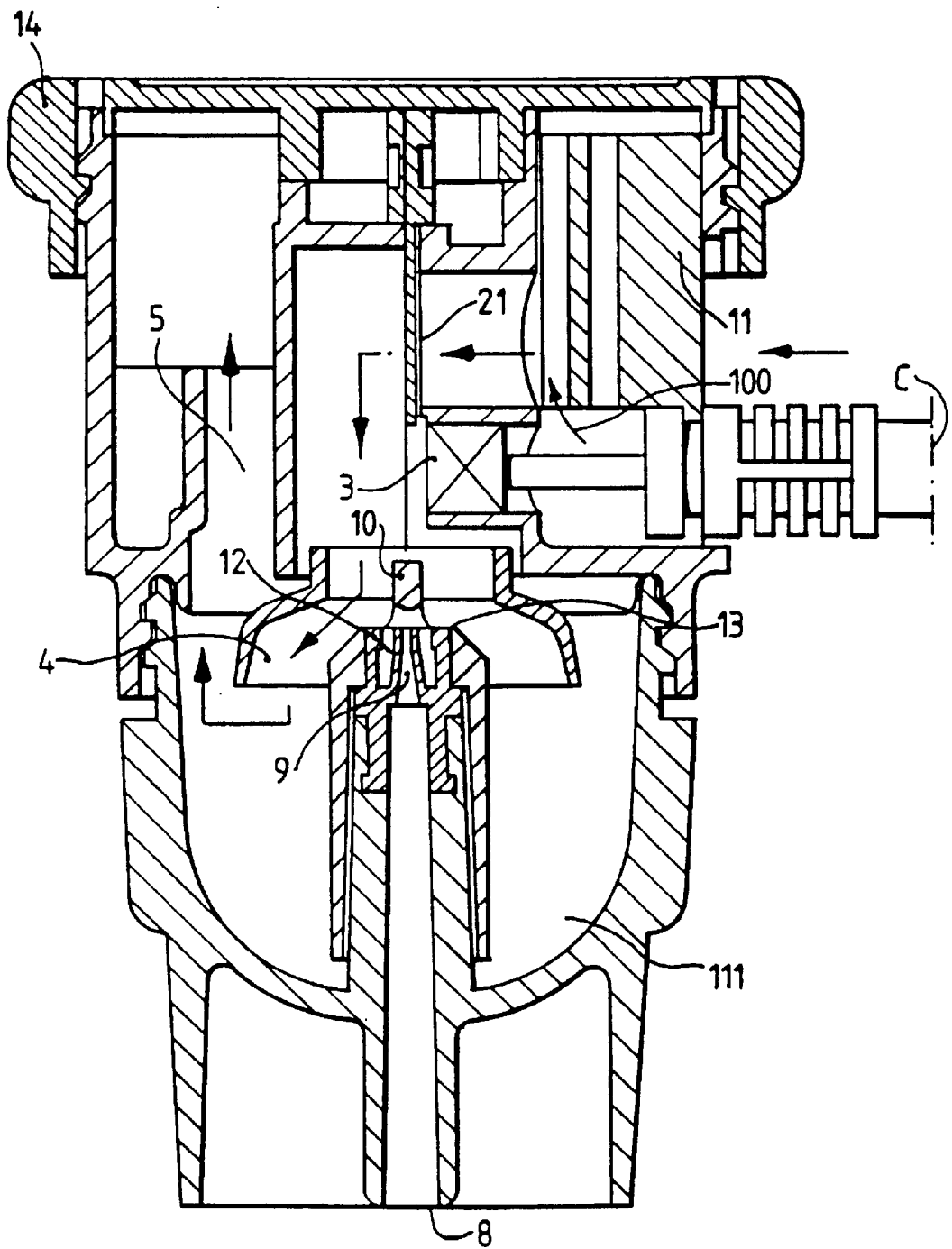
FIG. 4 is an axial cross-section taken at right angles to the cross-section of FIG. 2.

FIGS. 2, 3 and 4 shows an alternative valved delivery system in which the air flow is directed over a microphone 3 (FIG. 4) via a flap valve 21 only during inhalation and is directed in a different path during exhalation. The patient inhales and exhales through a mouthpiece port A (FIG. 2) and air is inhaled into the device via port C and exhaled from the device via port (B).

When the patient breaths in air it is drawn through port C, as indicated by arrow 100 (FIG. 4) and passes via a silencer baffle 11 to an inlet valve 21. The silencer baffle prevents nebulizer noise escaping and also isolates the microphone 3 form external noise. The silencer baffle can be replaced by a sealed filter where absolute system to atmosphere containment is required.

As the air passes through inlet valve 21 the resulting turbulence is detected by the microphone 3 and the air then passes through a liquid drug nebulizer baffle 4 and up via port 5 to the patient at port A (FIG. 2). When the patient breaths out the air passes via gallery 6 (FIGS. 2 and 3) to an exhalation valve 7 which is shown as a flexible flap valve. The air then exits via port B to the atmosphere. The gallery 6 prevents any liquid in the airstream of the patient from returning to the nebulizer reservoir; instead any such liquid passes out through the exhalation valve 7. An exhalation filter can be connected to port B if required.

Figure 5:
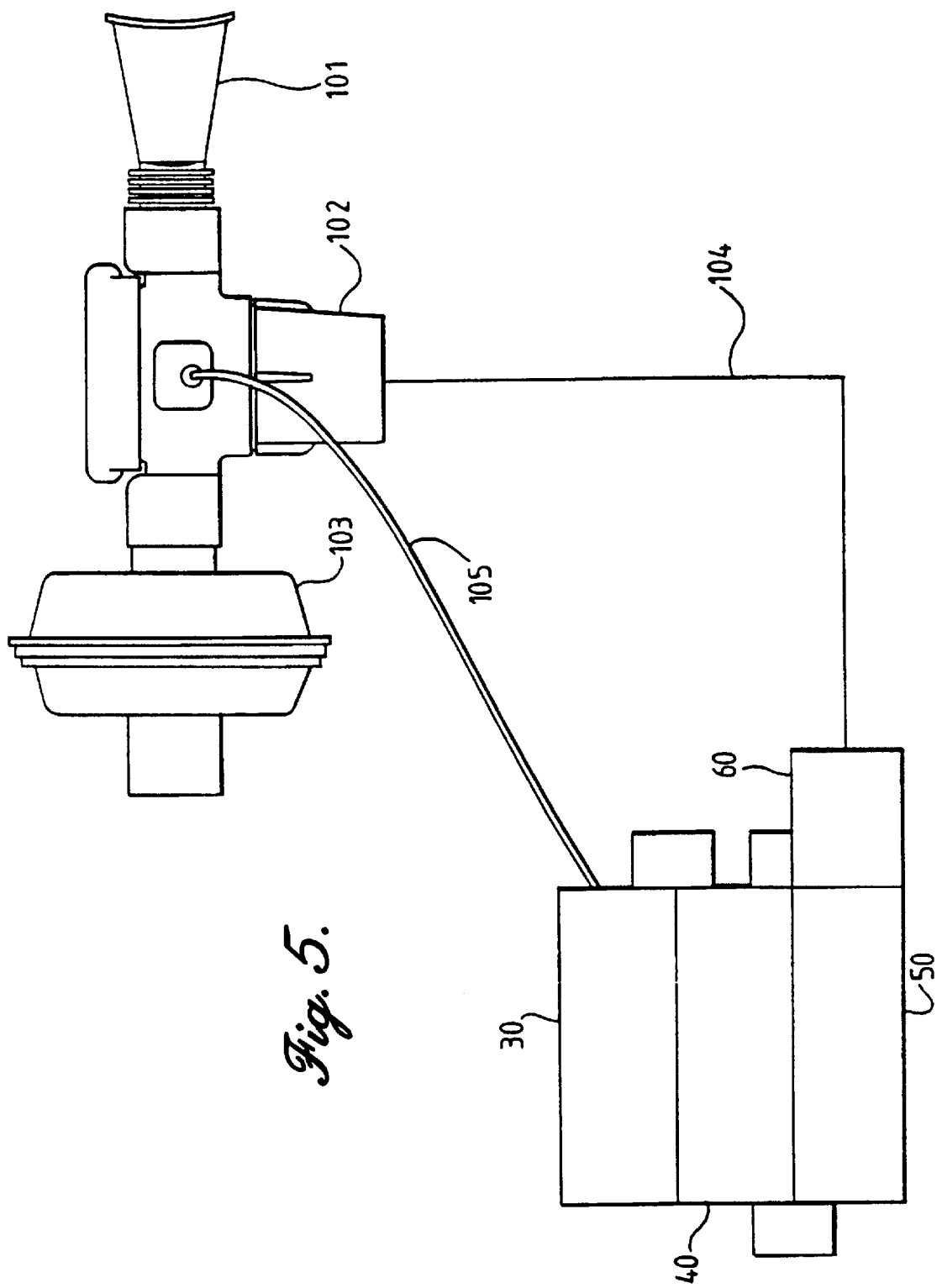
FIG. 5 is a schematic representation of a further embodiment utilizing a remotely located sensor.

When the microphone detects the turbulence during the inhalation phase of the breathing cycle, the nebulizer is supplied with compressed air via an inlet connector 8 (FIG. 4) under the control of a solenoid valve (FIG. 5). The schematic representation of FIG. 5 of the overall system (described more fully later), shows the sensor remotely located, however the system is equally applicable to a sensor mounted in the mouthpiece (see FIG. 1) or in a valved system (See FIGS. 2, 3 and 4). The compressed air passes through a jet 9 at high velocity and strikes a bar 10 which divides the air flow into two high velocity horizontal streams. These two high velocity horizontal streams generate a low pressure area above a reservoir 111 which draws liquid into liquid jets 12. The liquid from these jets is spread out into a thin film and formed into small particles at edge 13. Particles larger than a predetermined size (e.g. 5 micro meters) impact on a baffle 4 whereas smaller particles of the desired size are drawn down and out of the nebulizer by air flow through the baffle. This nebulizer design is shown in more detail in the above-mentioned GB 838453 and GB 1283988 which are incorporated herein by reference.

The microphone 3 is an ultra miniature electret condenser microphone (having a frequency response of 50 Hz to 84 Khz) and is desirably mounted close to the valve flap 21.

The delivery system is fully reusable, and in particular it will be noted that it includes a screwed cap 14 which can be unscrewed and removed to gain access to the inlet valve 21 and exhalation valve 7. These can be removed, together with the microphone 3 which is locked in position. Once the microphone is removed all the other components can be cleaned in hot water (>65° C.) or autoclaved.

FIG. 5 shows an alternative embodiment comprising a mouthpiece 101, a valved delivery system and nebulizer arrangement 102 (which is similar but not identical to that shown in FIGS. 2 to 4) and a filter 103 which is connected to an exhalation port of the valved delivery system 102. The delivery system 102 differs from that shown in FIGS. 2 to 4 in that the microphone is mounted remotely in a sensor unit 30 and is connected to the delivery system 102 by a flexible tube 105. The mouth of the tube is located near a valve flap (not shown) in an inlet of the valved delivery system (102) and noise generated at this inlet is transferred along the tube to the microphone in the sensor unit 30. An airline 104 supplies compressed air to the nebulizer and is controlled by a solenoid valve 60 under the control of a control unit 40. The unit also includes a compressor 50 to supply the compressed air.

An electronic control system which can be used to control the above-described arrangement will now be described with reference to FIG. 6.

Figure 6:
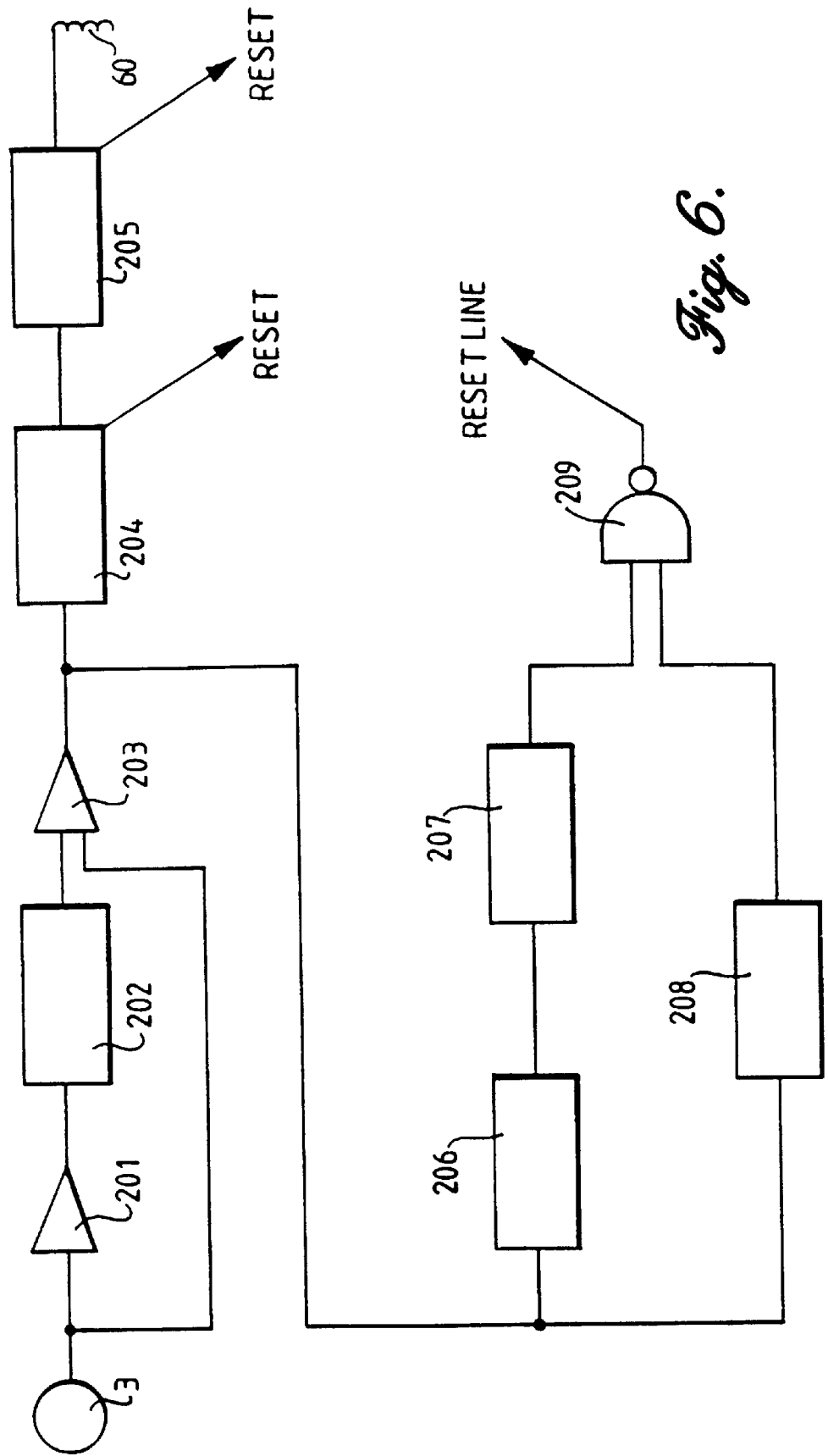
FIG. 6 is a block diagram of a control circuit for controlling the valved delivery system of FIGS. 2 to 4 or FIG. 5.

FIG. 6 shows a microphone 3 connected directly to one input of a comparator 203 and indirectly via an amplifier 201 and a smoothing circuit 202 to the other input of the comparator. Accordingly the comparator 203 generates an output signal only when a sudden fluctuation in the output of microphone 3 occurs (due to turbulence at the beginning of inhalation) and does not generate a signal when the microphone detects only normal ambient noise due to the air compressor 50 (FIG. 5) for example. The output of comparator 203 feeds a monostable multivibrator 204 which has a non-retriggerable period of three seconds and accordingly generates a higher output for three seconds, thereby triggering a monostable multivibrator 205 for a period of one second and opening the solenoid valve 60 for one second. Each of these multi vibrators is triggered by the positive edge of the input wave form and they may be constituted by a type 4538 dual multi vibrator for example.

In order to prevent the multi vibrators 204 and 205 from being energised by a momentary signal due to a sudden ambient noise, for example a gating circuit is provided, comprising a NAND gate 209 having one input coupled via a single retriggerable monostable multivibrator 208 to the output of comparator 203 and having its other input coupled to a similar retriggerable monostable multivibrator 207 whose input is in turn, connected to the output of a further monostable multivibrator 206, whose input is also connected to the output of comparator 203. The output of gate 209 is connected to reset terminals of monostable multivibrators 204 and 205.

Monostable multivibrators 206 and 207 form a delay mono stable arrangement. Monostable 206 is triggered by comparator 203 producing a 20 ms positive going pulse. The negative edge of this pulse triggers monostable 207 which produces a positive going 2 ms pulse. A 2 ms pulse is therefore, generated 20 ms after the trigger from comparator 203 is received. If, during this 20 millisecond period the continuous series of pulses form the output of comparator 203 has ceased (indicating that merely ambient noise and not turbulence was detected) then the output of monostable multivibrator 208 will be HIGH NAND gate 209 will generate an output signal which will reset the monostable multivibrators 204 and 205 and inhibit the operation of the nebulizer. The performance of the circuit will be understood by reference to the timing diagram FIG. 7.

Figure 7B:
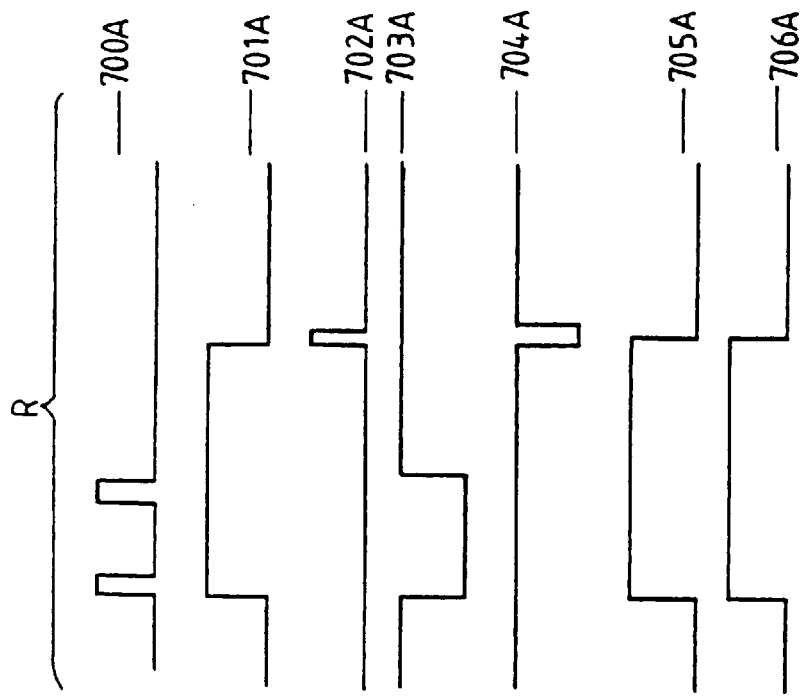
FIG. 7 is a timing diagram.
Figure 7A:
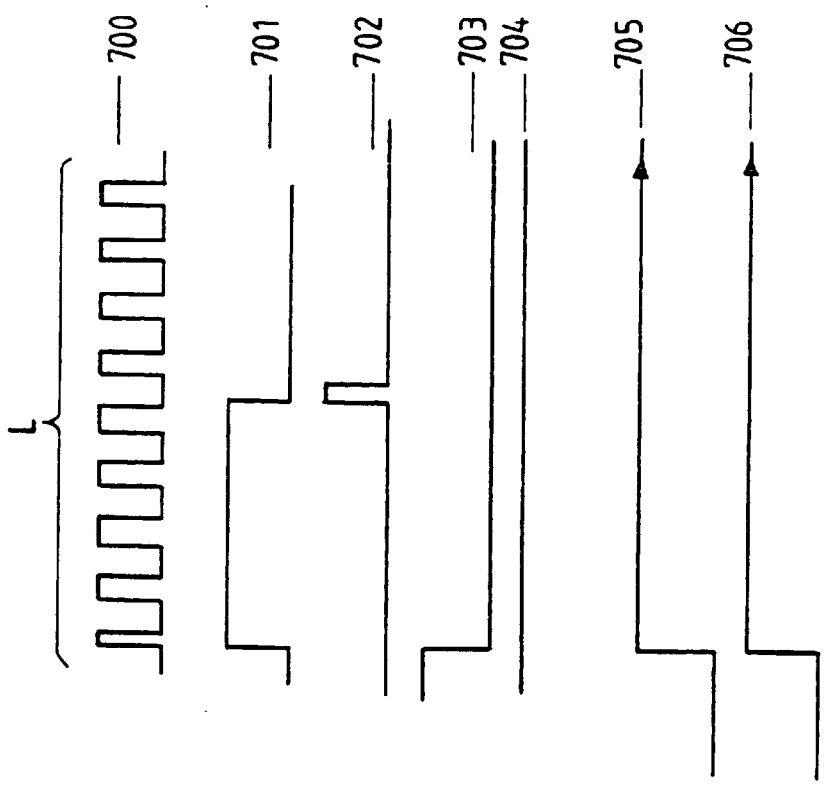

Referring to FIG. 7 in which the left hand side L represents the true trigger timing sequence whereas the right hand side R represents a false trigger timing sequence.

On left hand side L:- line 700 represent the output of the comparator 203 having a sequence spacing of less than 2 ms;

line 701 represents the sequence of the monostable 206 having a 20 ms vibration period;

line 702 represents the sequence of the monostable 207 producing a 2 ms pulse which is generated 20 ms after the trigger from the comparator 203 is received.

lines 203/704 represent the timing relationship between the monostable 208 and the NAND gate 209 which generate an output signal which will reset the monostable vibrators 204 and 205 after 3 seconds and 1 second respectively as shown at lines 705 and 706.

A sequence of false trigger timing is shown at R in FIG. 7 in which corresponding lines for the false trigger are allocated the same line numbers as under L but qualified by A.

The sequence is relative to a 20 ms vibration period of the monostable 206 which is reflected in the same vibration period for monostable 204 and 205 with a negative 10 ms pulse of monostable 208 as well as positive and negative 2 ms pulse for monostable 207 and 209 coincident with the end of the 20 ms vibration period of the monostable 206.

The arrangement is set to give a predetermined number of doses of drug aerosol, one during each inhalation phase of the breathing cycle of the patient, each dose cycle taking a minimum of three seconds, corresponding to 20 breaths per minute. This allows for stable operation, with a nominal nebulizer operation period of one second and a nominal two second pause to recharge the nebulizer driving system.

What is claimed is:

1. A drug delivery arrangement for delivering a drug aerosol to the respiratory system of a patient, comprising:
   a) duct means having a first inlet, the first inlet being open to the atmosphere, the duct means being arranged to convey from said first inlet an airstream inhaled by the patient;
   b) nebulizer means communicating with said duct means and arranged to generate a drug aerosol in said airstream, said nebulizer means having a second external inlet for connection to a compressed air supply;
   c) means for generating turbulence in said airstream due to inhalation by the patient;
   d) a microphone selectively responsive to said turbulence due to inhalation to generate a control signal; and
   e) control means coupled to said nebulizer means and responsive to said control signal to cause said nebulizer means to generate said aerosol selectively during said inhalation phase of the breathing cycle.

2. A drug delivery arrangement according to claim 1, which comprises a directional valve which is located in the path of and operated by said airstream and arranged to direct the airstream to said microphone during a predetermined phase of the breathing cycle.

3. A drug delivery arrangement according to claim 1, wherein the turbulence generating means comprises a chamber in which the microphone is located, the chamber having an aperture that is exposed to forward and reverse airflow of said airstream during the inhalation and exhalation phases of the breathing cycle and is so disposed that it responds selectively to either the forward or reverse airflow of said airstream, the aperture being approximately parallel to the axis of the airflow.

4. A drug delivery arrangement according to claim 1, wherein said control means is arranged to smooth the output of said microphone, to compare the instantaneous output of the microphone with the smoothed output of the microphone and to generate said control signal in response to the comparison of said outputs.

5. A drug delivery arrangement according to claim 1, wherein said control means is responsive to changes in the amplitude of the output of the microphone so as to mitigate the effects of continuous background noise.

6. A drug delivery arrangement according to claim 1, wherein said control means includes gating means which is arranged to inhibit the generation of said control signal unless said microphone generates an output signal for longer than a predetermined period.

7. A drug delivery arrangement according to claim 6, wherein said gating means includes a non-retriggerable monostable multivibrator and a retriggerable monostable multivibrator connected to a common input and having their outputs connected to respective inputs of a logic gate.

8. A drug delivery arrangement according to claim 1, wherein said microphone is coupled by a flexible tube to a further tube through which the patient breathes.

9. A method of delivering a drug aerosol to the respiratory system of a patient, comprising the steps of:
 a) generating turbulence in an airstream inhaled by a patient;
 b) selectively detecting said turbulence due to inhalation with a microphone and generating a control signal in response thereto; and
 c) in response to said control signal selectively generating a drug aerosol in said airstream during the inhalation phase of a patient's breathing cycle.

10. A method as claimed in claim 9, wherein said airstream is conveyed through a duct which has an inlet open to the atmosphere.

\* \* \* \* \*